United States Patent [19]

Drake

[11] Patent Number: 4,668,654

[45] Date of Patent: May 26, 1987

[54] NICKEL-CERIUM OXIDE-ZIRCONIUM OXIDE-SILICA CATALYSTS FOR HYDROGENATION OF SUCCINIC ANHYDRIDE TO BUTYROLACTONE

[75] Inventor: Charles A. Drake, Bartlesville, Okla.

[73] Assignee: Phillips Petroleum Company, Bartlesville, Okla.

[21] Appl. No.: 884,843

[22] Filed: Jul. 11, 1986

Related U.S. Application Data

[62] Division of Ser. No. 734,510, May 16, 1985, Pat. No. 4,620,017.

[51] Int. Cl.$^4$ .................... B01J 23/76; B01J 23/10; B01J 21/06; C07D 307/32
[52] U.S. Cl. .................... 502/242; 502/259; 502/263; 549/325
[58] Field of Search ............... 502/242, 263, 259, 304, 502/73; 549/325, 508

[56] References Cited

U.S. PATENT DOCUMENTS

| | | | |
|---|---|---|---|
| 3,257,163 | 6/1966 | Stiles | 23/2 |
| 3,264,226 | 8/1966 | Johnson | 252/465 |
| 3,395,004 | 7/1968 | Taylor et al. | 502/269 |
| 3,410,661 | 11/1968 | Taylor et al. | 502/259 |
| 3,469,967 | 9/1969 | Meddings et al. | 75/5 |
| 3,586,732 | 6/1971 | Guth et al. | 260/683.3 |
| 3,591,649 | 7/1971 | Kroll et al. | 260/667 |
| 4,002,658 | 1/1977 | Dalla-Betta et al. | 502/337 |
| 4,363,750 | 12/1982 | Rozovsky et al. | 502/242 |
| 4,539,310 | 9/1985 | Leftin et al. | 502/304 |

FOREIGN PATENT DOCUMENTS

| | | | |
|---|---|---|---|
| 49-9463 | 3/1974 | Japan | 549/325 |
| 49-9464 | 3/1974 | Japan | 549/508 |
| 49-16423 | 4/1974 | Japan | 549/325 |

Primary Examiner—P. E. Konopka
Attorney, Agent, or Firm—K. K. Brandes

[57] ABSTRACT

A process for preparing primarily gamma-butyrolactone comprises the step of contacting under suitable reaction conditions a succinic anhydride containing feed stream and hydrogen, in the presence of a catalyst composition comprising (a) substantially metallic nickel, (b) at least one oxide selected from oxides of cerium and zirconium, and (c) a silica-containing support. In another embodiment, the above described catalyst composition is provided.

28 Claims, No Drawings

NICKEL-CERIUM OXIDE-ZIRCONIUM OXIDE-SILICA CATALYSTS FOR HYDROGENATION OF SUCCINIC ANHYDRIDE TO BUTYROLACTONE

This application is a division of application Ser. No. 734,510, filed May 16, 1985, now U.S. Pat. No. 4,620,017.

BACKGROUND OF THE INVENTION

This invention relates to a process for preparing gamma-butyrolactone by hydrogenation of succinic anhydride. In another aspect, this invention relates to a catalytic process for making gamma-butyrolactone.

Processes for the catalytic hydrogenation of succinic anhydride to gamma-butyrolactone are known. U.S. Pat. Nos. 3,312,718 and 3,829,448 disclose hydrogenation processes employing nickel-based catalysts. However, there is an ever present need to develop new processes utilizing catalysts that are highly selective for the production of gamma-butyrolactone, thus minimizing the formation of undesirable by-products.

SUMMARY OF THE INVENTION

It is an object of this invention to provide a catalytic process for selectively hydrogenating succinic anhydride to gamma-butyrolactone. It is another object of this invention to provide a process employing new nickel-based hydrogenation catalysts that are more selective to making gamma-butyrolactone than previously known nickel-based catalysts. It is a further object to provide novel supported nickel catalysts. Other objects and advantages will be apparent from the detailed description and the appended claims.

In accordance with the present invention, a feed stream comprising succinic anhydride is contacted with a free hydrogen containing gas in the presence of a catalyst composition comprising (a) nickel metal, (b) at least one oxide of at least one metal selected from the group consisting of cerium and zirconium and (c) a silica-containing support, under such reaction conditions as will result in a reaction product comprising gamma-butyrolactone as the major component. Preferably over 50 weight-% of the reaction product is gamma-butyrolactone. In one embodiment, a reactant stream comprising succinic anhydride is hydrogenated over one of the above-cited catalyst compositions at an elevated temperature and an elevated pressure. The catalyst composition utilized in this invention is superior to one comprising only nickel and silica in that a greater portion of the formed reaction product is gamma-butyrolactone. In a further embodiment, catalyst compositions are provided consisting of (a) nickel, (b) at least one oxide of at least one metal selected from the group consisting of cerium and zirconium and (c) a silica-containing support material.

DETAILED DESCRIPTION OF THE INVENTION

The catalyst composition employed in the process of this invention, namely the selective hydrogenation of succinic anhydride to primarily gamma-butyrolactone, is a composition comprising (a) substantially metallic nickel, (b) at least one oxide of at least one metal selected from the group consisting of cerium and zirconium, and (c) a silica-containing support. The preferred support is silica generally having a surface area of at least 50 m$^2$/g (as determined by the BET/N$_2$ method; ASTM D3037). Silica can be made by any known process such as vapor phase hydrolysis of silicon compounds or precipitation from a metal silicate solution.

It is within the scope of this invention to use combinations of silica and other inorganic refractory oxides such as aluminum oxide, aluminum phosphate, alumino-silicate, titanium dioxide, thorium dioxide, lanthanum oxide, magnesium oxide and the like. The preferred component (b) is cerium oxide (Ce$_2$O$_3$ and/or CeO$_2$) or ZrO$_2$ or mixtures thereof.

The catalyst composition can be prepared by any known method of providing substantially metallic nickel on a silica-containing support, in conjunction with cerium oxide (Ce$_2$O$_3$ or CeO$_2$ or a mixture of both) and/or zirconium oxide (ZrO$_2$). Preferably the silica-containing support material is first impregnated with an aqueous solution containing a suitable nickel compound such as a nickel(II) nitrate, plus either a cerium compound such as cerium(III) or (IV) nitrate or a zirconium compound such as zirconium (IV) nitrate or nitrates of both cerium and zirconium. The thus impregnated material is calcined at a temperature high enough for a period of time long enough to convert at least a portion of the metal compounds, preferably nitrates, to the corresponding oxides (nickel oxide and cerium oxide and/or zirconium oxide). The calcined material is then heated with a reducing gas such as hydrogen or carbon monoxide, preferably H$_2$, so as to substantially reduce the nickel oxide to nickel metal. Typical calcination conditions comprise about 300°–400° C. and about 1–5 hours. Typical reducing conditions comprise about 300°–600° C. and about 1–5 hours.

It is within the scope of this invention to employ other methods of depositing nickel and either cerium or zirconium on the silica-containing support. Non-limiting examples of such methods are: impregnation with a solution of one or more solvated metals; impregnation with decomposable metal compounds such as nickel carbonyl or zirconium acetylacetonate and subsequent decomposition by heating; and condensation of metal vapors on the support.

The nickel content (measured as nickel metal) in the catalyst compositions of this invention generally ranges from about 0.2 to about 50 weight-% Ni, preferably from about 1 to about 40 weight-%, and more preferably from about 10 to about 30 weight-%, based on the entire catalyst composition. The content of cerium oxide and zirconium oxide (measured as Ce and Zr metal) generally ranges from about 0.1 to about 20 weight-% (Ce plus Zr), preferably from about 0.5 to about 10 weight-% (Ce plus Zr), more preferably from about 1 to about 5 weight-% (Ce plus Zr), based on the entire catalyst composition. It is understood that either only oxides of Ce or only oxides of Zr or a mixture of oxides of Ce plus Zr may be present. The surface area (as determined by the BET/N$_2$ method; ASTM D3037) of the finished catalyst composition generally ranges from about 50 to about 400 m$^2$/g.

The feed stream to be hydrogenated in accordance with the process of this invention can be substantially pure succinic anhydride, or a mixture of succinic anhydride with an inert substance such as a paraffin or an inert gas, or a mixture of succinic anhydride and gamma-butyrolactone (the desired product), such as a recycle stream from which a portion of butyrolactone has been removed and to which fresh succinic anhydride has been added. The second reactant can be substantially pure hydrogen gas or a mixture of hydrogen gas and another suitable gas such as an inert gas.

The succinic anhydride containing feed stream, the free hydrogen containing gas stream and the catalyst composition of this invention can be contacted in any suitable manner. Said two streams can be added separately into a suitable reaction vessel and then be contacted in at least partially mixed form with the catalyst composition under suitable reaction conditions. Or the two streams can be premixed and then contacted with the catalyst composition under suitable reaction conditions so as to produce a reaction product comprising gamma-butyrolactone. The process of this invention can be a batch process or a continuous process. In a batch process the process ingredients (succinic anhydride stream, hydrogen stream and catalyst composition) are added in any order to a vessel, preferably equipped with agitating and heating means, and the ingredients are then kept in contact for a certain length of time under suitable reaction conditions so as to produce a product comprising gamma-butyrolactone. In this type of operation, the catalyst can be dispersed in the liquid feed stream (slurry operation) and contacted with hydrogen with agitation (e.g., by means of a mechanical mixer or static mixing means); or the liquid feed stream and hydrogen can be circulated through a fixed bed containing the catalyst composition. In a continuous process, which is presently preferred, the succinic anhydride containing feed stream and the free hydrogen containing gas stream can be passed, at least partially mixed, through a fixed bed containing the solid catalyst composition, under such conditions as will result in a product comprising gamma-butyrolactone. Optionally, an inert solvent can be present during the batch or continuous process.

Heating of the process ingredients is generally required to accomplish at least partial conversion (preferably exceeding 50%) of succinic anhydride to gamma-butyrolactone. Any suitable temperature that will cause and maintain a controllable reaction can be employed. Any feasible heating means can be utilized. It is within the scope of this invention to preheat one or more of the process ingredients before they are introduced into a reactor, which is heated to maintain a suitable temperature. Generally the reaction temperature exceeds about 120° C. and preferably ranges from about 180° C. to about 300° C.

The reaction pressure generally is above atmospheric pressure. The selection of the reaction pressure will greatly depend on the reaction temperature, the feed rates of liquid feed and, hydrogen and the specific reactor design. Generally the pressure ranges from about 100 to about 10,000 psig, preferably about 1,000 to about 3,000 psig.

The reaction time, i.e., the time of intimate, simultaneous contact of all process ingredients, can vary from 1 minute to about 50 hours and will preferably be in the range of about 0.2 to about 2 hours. The actual reaction time will greatly depend on the flow rates of the succinic anhydride containing feed stream and of the hydrogen containing gas stream, the selection of an effective, yet safe reaction temperature, the extent of mixing and agitation (if any) during the reaction, the amount of the catalyst employed, etc.

Any suitable molar ratio of hydrogen to succinic anhydride can be employed. Generally, an excess of hydrogen over what is stoichiometrically required is employed. The exact ratio that should be employed greatly depends on the reaction temperature, pressure and reaction time. Unreacted hydrogen is preferably separated from the reactor effluent and recycled to the hydrogenation reactor.

The formed reaction product, which comprises gamma-butyrolactone, can be separated from the reaction mixture by any suitable separation means such as fractional distillation, or crystallization, or extraction with a suitable solvent (e.g., a liquid paraffin such as n-hexane) plus subsequent evaporation of the solvent. Unreacted process ingredients, particularly succinic anhydride, are preferably at least partially separated in a similar manner and can be recycled to the reaction zone with added fresh ingredients. The utility of gamma-butyrolactone is disclosed in U.S. Pat. No. 4,083,809, herein incorporated by reference.

The following examples are presented to further illustrate this invention without unduly limiting the scope of the invention.

EXAMPLE I

This example illustrates the preparation of the nickel catalyst compositions employed in the catalytic hydrogenation of succinic anhydride.

Control Catalyst A was prepared by mixing 100 grams of G57 silica (BET/$N_2$ surface area: 300 $m^2$/g; pore volume: 1.0 cc/g; Na content: 0.1 weight-%; $Al_2O_3$ content: 0.05 weight-%; supplied by Davison Chemical Division of W. R. Grace, Inc., Baltimore, MD) with a solution of 100 grams of nickel nitrate in 60 mL $H_2O$. The thus impregnated silica is first partially dried under vacuum conditions in a rotating evaporator, then dried at about 100° C. for 1 hour in air, calcined at about 350° C. for 3 hours, and finally reduced by a flowing hydrogen stream at about 450° C. for 3 hours. Catalyst A had a nickel content of 20.2 weight-% Ni.

Control Catalyst B was prepared by adding to 50 grams of G-57 silica a mixture containing 50 grams of nickel nitrate, 5 grams of ammonium metatungstate and 30 mL of $H_2O$. Drying, calcining and reducing conditions were the same as for the preparation of Catalyst A. Catalyst B contained 20.2 weight-% Ni and 9.0 weight-% W.

Invention Catalyst C was prepared by adding to 50 grams of nickel nitrate, 5 grams of zirconium nitrate and 30 mL of water. Drying, calcining and reducing conditions were the same as those described for Catalyst A. Catalyst C contained 20.2 weight-% Ni and 3.7 weight-% Zr.

Invention Catalyst D was prepared by adding to 50 grams of G-57 silica a mixture containing 50 grams of nickel nitrate, 5 grams of cerium nitrate and 30 mL of water. Drying, calcining and reducing conditions were the same as described for catalyst A. Catalyst D contained 20.2 weight-% Ni and 3.2 weight-% Ce.

EXAMPLE II

This example illustrates the hydrogenation of succinic anhydride over the nickel catalysts described in Example I. A stainless steel pipe having an inner diameter of about 0.5 inch and a length of about 12 inches was filled with about 40 grams of a catalyst. The reactor was heated by means of electric furnace. A liquid feed stream containing 30 weight-% succinic anhydride and 70 weight-% gamma-butyrolactone was pumped downwardly through the reactor at a feed rate of 1.0 mL/minute. Hydrogen gas was introduced essentially simultaneously with the feed at a rate ranging from about 100 to about 500 Liter/hour. The reactor pressure was about 1500 psig. The liquid product was collected and distilled. The volatile fraction was analyzed by means of a Hewlett Packard Model 5880 gas chromatograph. Pertinent operating conditions and results are summarized in Table I.

TABLE I

| Run | Catalyst | Temp. (°C.) | H$_2$ Flow (L/Hr.) | % Conversion of Succ. Anhydride | % Selectivity[1] to Butyrolactone |
|---|---|---|---|---|---|
| 1 (Control) | A | 229 | 230 | 99 | 59 |
| 2 (Control) | B | 231 | 230 | 85 | 38 |
| 3 (Invention) | C | 212 | 230 | 100 | 95 |
|  | C | 210 | 450–500 | 100 | 97 |
|  | C | 213 | 450–500 | 100 | 97 |
| 4 (Invention) | D | 225 | 230 | 98 | 87 |
|  | D | 221 | 450–500 | 100 | 85 |
|  | D | 229 | 450–500 | 100 | 88 |

[1]Weight % of gamma-butyrolactone in the product divided by % conversion, multiplied by 100.

Data in Table I show that the incorporation of Zr or Ce into a silica-supported nickel catalyst had a significant beneficial effect on the %-selectivity to gamma-butyrolactone, whereas the incorporation of W into the Ni/SiO$_2$ catalyst had an adverse effect on the selectivity to gamma-butyrolactone.

Reasonable variations and modifications are possible within the scope of the disclosure and appended claims.

I claim:

1. A composition of matter consisting essentially of
   (a) nickel metal,
   (b) at least one of Ce$_2$O$_3$ and CeO$_2$,
   (c) ZrO$_2$, and
   (d) silica support.

2. A composition of matter in accordance with claim 1 having a surface area in the range of from about 50 to about 400 m$^2$/g.

3. A composition of matter in accordance with claim 1 having a nickel content in the range of from about 0.2 to about 50 weight-% Ni.

4. A composition of matter in accordance with claim 1 having a nickel content in the range of from about 10 to about 30 weight-% Ni.

5. A composition of matter in accordance with claim 1 having a (Ce+Zr) content in the range of from about 0.1 to about 20 weight-%.

6. A composition of matter in accordance with claim 1 having a (Ce+Zr) content in the range of from about 1 to about 5 weight-%.

7. A composition of matter consisting essentially of
   (a) nickel metal,
   (b) at least one cerium oxide,
   (c) zirconium oxide, and
   (d) silica support;
   wherein said composition of matter has been prepared by a process comprising the steps of
   (i) impregnating said silica support with an aqueous solution comprising at least one compound of nickel, at least one compound of cerium and at least one compound of zirconium;
   (ii) calcining the impregnated material obtained in step (i) at a temperature high enough and a period long enough to convert at least a portion of said at least one compound of nickel to nickel oxide, at least a portion of said at least one compound of cerium to cerium oxide, and at least a portion of said at least one compound of zirconium to zirconium oxide;
   (iii) heating the calcined material obtained in step (ii) with a reducing gas under such conditions as to reduce the nickel oxide to nickel metal.

8. A composition of matter in accordance with claim 7, wherein said at least one compound of nickel is nickel nitrate, said at least one compound of cerium is cerium nitrate, and said at least one compound of zirconium is zirconium nitrate.

9. A composition of matter in accordance with claim 7, wherein said reducing gas is hydrogen.

10. A composition of matter in accordance with claim 7, wherein said heating in step (iii) is carried out at about 300°–600° C.

11. A composition of matter in accordance with claim 7, wherein said silica support used in step (i) has a surface area of at least 50 m$^2$/g.

12. A composition of matter in accordance with claim 7, wherein said at least one cerium oxide (b) is selected from the group consisting of Ce$_2$O$_3$ and CeO$_2$, and said zirconium oxide (c) is ZrO$_2$.

13. A composition of matter in accordance with claim 7 having a surface area in the range of from about 50 to about 400 m$^2$/g.

14. A composition of matter in accordance with claim 7 having a nickel content in the range of from about 0.2 to about 50 weight-% Ni.

15. A composition of matter in accordance with claim 7 having a nickel content in the range of from about 10 to about 30 weight-% Ni.

16. A composition of matter in accordance with claim 7 having a (Ce+Zr) content in the range of from about 0.1 to about 20 weight-%.

17. A composition of matter in accordance with claim 7 having a (Ce+Ze) content in the range of from about 1 to about 5 weight-%.

18. A process for preparing a composition of matter consisting essentially of
   (a) nickel metal,
   (b) at least one cerium oxide,
   (c) zirconium oxide, and
   (d) silica support,
   wherein said process comprises the steps of
   (i) impregnating said silica support with an aqueous solution comprising at least one compound of nickel, at least one compound of cerium and at least one compound of zirconium;
   (ii) calcining the impregnated material obtained in step (i) at a temperature high enough and a period long enough to convert at least a portion of said at least one compound of nickel to nickel oxide, at least a portion of said at least one compound of cerium to cerium oxide, and at least a portion of said at least one compound of zirconium to zirconium oxide;

(iii) heating the calcined material obtained in step (ii) with a reducing gas under such conditions as to reduce the nickel oxide to nickel metal.

19. A process in accordance with claim 18, wherein said at least one compound of nickel is nickel nitrate, said at least one compound of cerium is cerium nitrate, and said at least one compound of zirconium is zirconium nitrate.

20. A process in accordance with claim 18, wherein said reducing gas is hydrogen.

21. A process in accordance with claim 18, wherein said heating in step (iii) is carried out at about 300°–600° C.

22. A process in accordance with claim 18, wherein said silica support used in step (i) has a surface area of at least 50 m²/g.

23. A process in accordance with claim 18, wherein said at least one cerium oxide (b) is selected from the group consisting of $Ce_2O_3$ and $CeO_2$, and said zirconium oxide (c) is $ZrO_2$.

24. A process in accordance with claim 18, wherein said composition of matter has a surface area in the range of from about 50 to about 400 m²/g.

25. A process in accordance with claim 18, wherein said composition of matter has a nickel content in the range of from about 0.2 to about 50 weight-% Ni.

26. A process in accordance with claim 18, wherein said composition of matter has a nickel content in the range of from about 10 to about 30 weight-% Ni.

27. A process in accordance with claim 18, wherein said composition of matter has a (Ce+Zr) content in the range of from about 0.1 to about 20 weight-%.

28. A process in accordance with claim 18, wherein said composition has a (Ce+Zr) content in the range of from about 1 to about 5 weight-%.

* * * * *